United States Patent
Sugimoto et al.

(10) Patent No.: US 10,241,012 B2
(45) Date of Patent: Mar. 26, 2019

(54) METHOD FOR DILUTED PLASMA SEPARATION USING CONTAINER FOR BLOOD DILUTION AND STORAGE CONTAINING GELLING AGENT FOR PLASMA SEPARATION

(71) Applicant: Leisure, Inc., Tokyo (JP)

(72) Inventors: Shinya Sugimoto, Tokyo (JP); Isao Yonekubo, Tokyo (JP); Masato Kawaguchi, Tokyo (JP); Susumu Osawa, Chiba (JP)

(73) Assignee: Leisure, Inc., Tokyo (JP)

( * ) Notice: Subject to any disclaimer, the term of this patent is extended or adjusted under 35 U.S.C. 154(b) by 0 days.

(21) Appl. No.: 15/318,084

(22) PCT Filed: Jun. 12, 2014

(86) PCT No.: PCT/JP2014/065628
§ 371 (c)(1),
(2) Date: Dec. 12, 2016

(87) PCT Pub. No.: WO2015/189961
PCT Pub. Date: Dec. 17, 2015

(65) Prior Publication Data
US 2017/0131189 A1    May 11, 2017

(51) Int. Cl.
*G01N 1/00* (2006.01)
*G01N 1/38* (2006.01)
(Continued)

(52) U.S. Cl.
CPC ............. *G01N 1/38* (2013.01); *A61B 5/14* (2013.01); *A61B 10/0096* (2013.01);
(Continued)

(58) Field of Classification Search
None
See application file for complete search history.

(56) References Cited

U.S. PATENT DOCUMENTS

| | | | |
|---|---|---|---|
| 4,867,887 A | 9/1989 | Smith | |
| 6,835,353 B2 * | 12/2004 | Smith | ............... B01L 3/5021 210/416.1 |

(Continued)

FOREIGN PATENT DOCUMENTS

| | | |
|---|---|---|
| CN | 102438757 | 5/2012 |
| JP | H08108096 | 4/1986 |

(Continued)

OTHER PUBLICATIONS

Supplemental European Search Report dated Dec. 21, 2017 relating to co-pending European Patent Application No. 14894697.3—3 Pages.

(Continued)

*Primary Examiner* — Jyoti Nagpaul
(74) *Attorney, Agent, or Firm* — McCarter & English, LLP

(57) ABSTRACT

A method for separating plasma in a minute amount of a blood sample diluted with a blood dilution buffer is provided. When a blood dilution buffer is added to a minute amount of blood (about 20 to 100 μL) so as to assay the biological blood components in the resulting diluted plasma, it is necessary to separately store and transfer the diluted blood cell component and the diluted plasma component. The present inventors found that it is possible to separate diluted plasma from diluted blood cells using a polymer gelling agent for plasma separation by means of putting a polymer gel for plasma separation in the container with a blood dilution buffer. In such case, diluted blood cells are transferred to the lower portion of the polymer gelling agent and dilute plasma is transferred to the upper portion of the same. Assay of the biological blood components using a minute amount of blood can be utilized for early detection of health status, diseases, and presymptomatic states. The (Continued)

method is advantageous in that it is not limited in terms of time or location for blood collection.

15 Claims, 6 Drawing Sheets

(51) Int. Cl.
| | |
|---|---|
| *G01N 33/48* | (2006.01) |
| *G01N 1/20* | (2006.01) |
| *G01N 33/49* | (2006.01) |
| *A61B 10/00* | (2006.01) |
| *A61B 5/145* | (2006.01) |
| *B01L 3/00* | (2006.01) |

(52) U.S. Cl.
CPC ............ *B01L 3/50215* (2013.01); *G01N 1/20* (2013.01); *G01N 33/48* (2013.01); *G01N 33/491* (2013.01); *G01N 2001/381* (2013.01)

(56) References Cited

U.S. PATENT DOCUMENTS

| | | |
|---|---|---|
| 2002/0153316 A1 | 10/2002 | Nanba et al. |
| 2003/0175167 A1* | 9/2003 | Takanori ................. B01L 3/502 422/534 |
| 2004/0129631 A1 | 7/2004 | Anraku et al. |
| 2012/0053041 A1 | 3/2012 | Ihm et al. |
| 2014/0360944 A1* | 12/2014 | Esteron ................. A61K 35/14 210/698 |

FOREIGN PATENT DOCUMENTS

| | | |
|---|---|---|
| JP | H02134564 | 5/1990 |
| JP | H07294516 | 11/1995 |
| JP | H08201391 | 8/1996 |
| JP | 2001255323 | 9/2001 |
| JP | 2003294731 | 10/2003 |
| WO | 2013/111130 | 8/2013 |

OTHER PUBLICATIONS

International Search Report relating to co-pending International Application No. PCT/JP2014/065628, dated Sep. 16, 2014—2 Pages.

Chinese Office Action based on co-pending Chinese Application No. 201480079806.2 dated Jun. 26, 2018—2 Pages.

* cited by examiner

○ A type of structure wherein the gelling agent for plasma separation is enclosed within the bottom portion above the dilution buffer

METHOD FOR DILUTED PLASMA SEPARATION USING CONTAINER FOR BLOOD DILUTION AND STORAGE CONTAINING GELLING AGENT FOR PLASMA SEPARATION

RELATED APPLICATIONS

This application is a national stage application filed under 35 USC 371 of PCT/JP2014/065628, flied Jun. 12, 2014, all of which are incorporated herein, in entirety, by reference.

TECHNICAL FIELD

The present invention relates to a method for separating plasma from a blood sample obtained by diluting a minute amount of blood with a blood dilution buffer.

BACKGROUND ART

A method for separating collected blood into blood cells and plasma has been known in the art (e.g., JP Patent Publication (Kokai) No. H7-294516 A (1995)).

Known examples of separating agents used in such blood separation operations include a polymer compound for forming separate layers (a) such as a silicone oil, chlorinated polybutene, polyisobutene, an acrylic polymer, a copolymer of α-olefin having 6-20 carbon atoms and dimethyl maleate, and styrene.dimethyl maleate copolymer as a main component, mixed with a thixotropic agent (b). Such compositions have been used in practice.

Known examples of thixotropic agents include inorganic fine powders (silica, clay, and the like), and organic gelling agents such as a condensation product of sorbitol and benzaldehyde (dibenzylidene sorbitol), hydrogenated castor oil, 12-hydroxy stearic acid, a nitrohumic acid adduct of water-soluble protein, glutamic amide, dimethanol octahydronaphthalene copolymer for the control of specific gravity and viscosity.

Further, a method for accommodating a previously collected blood sample in a container together with a blood dilution buffer and assaying biological components of such blood sample in such container has been conventionally known.

Assay of the biological blood components using a minute amount of blood in a container accommodating such previously collected blood sample can be utilized for early detection of health status, diseases, and presymptomatic states.

This approach is advantageous in that the time and location at which blood is collected for blood testing can be freely determined.

In the above case, it is necessary to transfer the container containing the collected blood sample from the site of collection to the site of sample analysis. That is, it becomes necessary to accommodate and store the blood sample in a container according to the present invention. In order to obtain accurate analytical results for a collected blood sample, it is essential to minimize changes in the state of the blood sample by keeping it in a container together with a dilution buffer during storage.

One known method for storing a blood sample is a method comprising diluting blood with a blood dilution buffer containing an internal standard, separating the diluted blood cell component from the diluted plasma component via a filter (i.e., filtration means), and storing the resultant in a container (see, e.g., JP Patent Publication (Kokai) No. 2001-255323 A).

SUMMARY OF INVENTION

Technical Problem

However, blood cell separation via a filter requires the application of physical pressure. This may cause hemolysis of such blood cells due to physical pressure, making it impossible to accurately assay the diluted plasma component.

In order to assay the biological components of a minute amount of blood, it has been required to dilute blood 5- to 10-fold with a blood dilution buffer containing an internal standard and separate the diluted blood cell component from such blood via a filter. Physical pressure is applied during such separation of blood cells via a filter, thus causing hemolysis of blood cells. This sometimes results in failure to accurately assay the diluted plasma component due to an increase in the plasma dilution factor and interference from hemoglobin upon assay. Further, diluted plasma remains in the filter, causing a decrease in the amount of recovered diluted plasma and requiring re-dilution. This has been problematic because of the resulting reduction of accuracy.

When separating a diluted plasma component from a blood sample via a filter, physical pressure causes blood cells to rupture during filtration, resulting in hemolysis. Therefore, it has been necessary to increase the osmotic pressure of the blood dilution buffer so as to make blood cells contract, which in turn prevents hemolysis. In such cases, moisture is released from blood cells into the plasma, resulting in erroneous component assay. Therefore, a measurement coefficient must to be set for each test item. This has been problematic.

Also, conventional methods for separating blood cells from plasma by centrifuging a blood sample using a polymer gel have been problematic because of the relatively poor separation efficiency resulting from a slight difference in specific gravity between blood cells and plasma. Some blood cells remain in the plasma and become hemolyzed during preservation, impacting assay.

Solution to Problem

In consideration of the above circumstances, the present inventors found a technique for effectively separating and separately storing blood cells and diluted plasma in a container containing a blood dilution buffer and using a polymer gel for plasma separation. A blood dilution buffer is added to a minute amount of collected blood (about 20 to 100 μL) and separation is carried out such that the diluted blood cells are transferred to the lower region of the polymer gelling agent while the diluted plasma is transferred to the upper region of the same.

According to the present invention, a method for centrifuging a sample obtained by diluting a minute amount of blood with a dilution buffer with the use of a polymer gel for plasma separation is provided. In addition, a container for dilution and storage of a minute amount of blood accommodating a polymer gel for plasma separation is provided.

According to the present invention, a container for blood dilution and storage is prepared. The container is used for separation of blood cells from diluted plasma via centrifugation.

Both a dilution buffer for diluting plasma in blood and collected blood are injected into the aforementioned container.

Further, a predetermined amount of polymer gel having a specific gravity falling between the specific gravity of the blood cells and that of the diluted plasma is introduced into the container. Thus, the container accommodates both the dilution buffer and the polymer gel.

In the above case, the blood dilution buffer and the polymer gelling agent for plasma separation coexist in the same container and are allowed to come into direct contact with each other, although they are not allowed to mix. That is, the blood dilution buffer and the polymer gelling agent for plasma separation separately occupy different regions in the same container.

In one embodiment, the dilution buffer forms a layer beneath a sealing cap for the upper opening of the container, and the polymer gelling agent for plasma separation forms a layer thereunder.

In another embodiment, the polymer gelling agent for plasma separation forms a layer on the upper opening side, and the dilution buffer forms a layer thereunder.

Then, a collected blood sample is introduced from the upper opening into the container accommodating the both the agent and the buffer. A centrifugal force is applied to the container in a downward direction. This results in separation of the blood sample into blood cells and plasma both diluted with the dilution buffer. In such case, a centrifugal force of about 1300 G is applied to the container for about 10 minutes.

In a preferred embodiment, the specific gravity of the dilution buffer is lower than the specific gravity of plasma. The specific gravity of the plasma diluted with the dilution buffer becomes about 1.012 to 1.014. That is, the difference in specific gravity between the blood cells and the diluted plasma is increased. Therefore, the separation of diluted blood cells and diluted plasma becomes easier than the separation of undiluted blood cells (which have a specific gravity of about 1.095) and undiluted plasma (which have a specific gravity of about 1.027). A diluent used herein is a liquid having a specific gravity of about 1.0106 and an osmotic pressure of about 285 mOsm/L, thus making such diluent isotonic with blood. When the dilution buffer has a high osmotic pressure, the osmotic pressure is about 500 mOsm/L and the specific gravity is about 1.011. Preferably, the container for accommodating a blood sample is made of clear plastic.

Preferably, a mark is made on the container, and the mark indicates that the container is filled with a predetermined amount of blood. In such case, it is preferable to make such mark on the outer circumference of the container containing the blood dilution buffer at a location such that the mark indicates that the container is filled with 20 to 100 μL (e.g., about 65 μL) of blood, thereby making it possible to visually confirm the collection of a predetermined amount of blood. Preferably, the upper opening of the container can be opened or closed using a tightly sealable cap, such as a screw-type cap, which improves sealing performance. Further, the bottom portion of the container may be openable/closable or detachable. Such configuration allows a centrifugal force to be applied to the container containing the blood dilution buffer, thereby removing sedimented blood cells adhering to the bottom portion and allowing such cells to be used for an examination (utilizing blood cells) of glycated hemoglobin in relation to diabetes and the like. The cap used for such bottom portion preferably has a shape that is compatible with a container that can be used for blood cell dilution, additionally allowing the container to be used for a diluted hemolysate. Therefore, the resulting blood analysis structure can be directly used for the examination of glycated hemoglobin without modification.

For example, the container has a cylindrical shape and is 14±2 mm in outer diameter and 75±5 mm in height. It is configured so as to have a bottom portion provided with a detachable cylindrical bottom cap 14±2 mm in outer diameter and 25±2 mm in height. The inner space of the container is shaped such that it has an uppermost portion having an inner diameter of 10 mm and a lowest bottom portion having an inner diameter of 5 mm, the depth from the uppermost portion to the lowest bottom portion is 30 mm, and the shape of the inner space tapers from the uppermost portion toward the lowest bottom portion.

In such case, the inner portion of the blood collection container has an upper inner circle diameter of 10 mm, a depth of 30 mm, and an inner bottom diameter of 5 mm. It has an inverted conical shape that tapers downward toward the bottom.

The composition of the polymer gel for plasma separation comprises, for example, a thixotropic-gel-type separating agent obtained by kneading a cyclopentadiene resin, dibenzylidene sorbitol, silica, and phthalic acid (2-ethylhexyl) (JP Patent Publication (Kokai) No. H7-294516 A (1995)). Alternatively, it may comprise a similar thixotropic-gel-type separating agent.

The physical properties of the polymer gel for plasma separation are as follows: HLB value: 4.02 to 9.0; specific gravity: 1.02 to 1.08 at 25° C.; and molecular weight distribution determined by the GPC method for molecular weight: 700-850.

Such gel-type separating agent is characterized in that diluted plasma can be separated from blood cells under conditions in which a centrifugal force of 1,300 G is applied for 10 minutes.

Advantageous Effects of Invention

The present invention is intended to separate diluted plasma used as a sample, the specific gravity of which is lower than that of undiluted plasma, thereby improving the efficiency of separation of blood cells. Further, it is possible to accurately examine collected blood because there is no risk of destroying blood cells.

DESCRIPTION OF EMBODIMENTS

Figure 1:
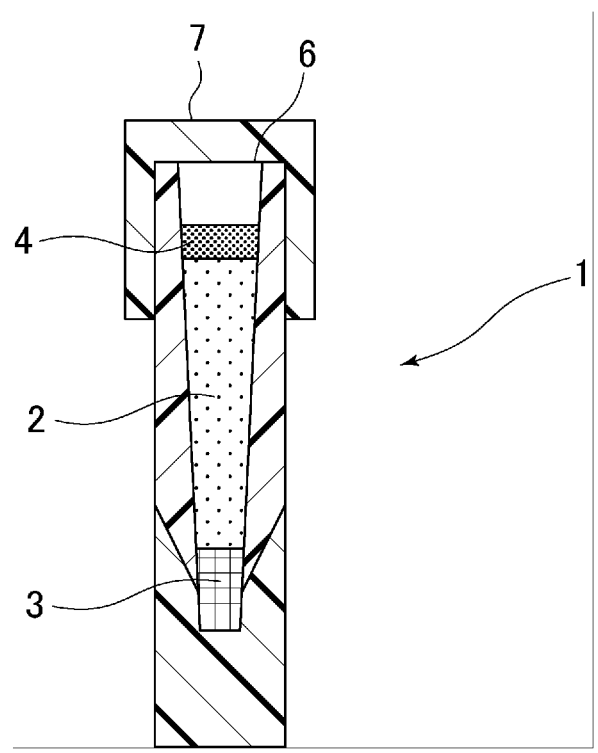
FIG. 1 schematically shows a cross-sectional view of the blood analysis structure in which a dilution buffer and a gelling agent for plasma separation are layered in accordance with the present invention when the container for blood dilution and storage accommodates collected blood.
Figure 2:
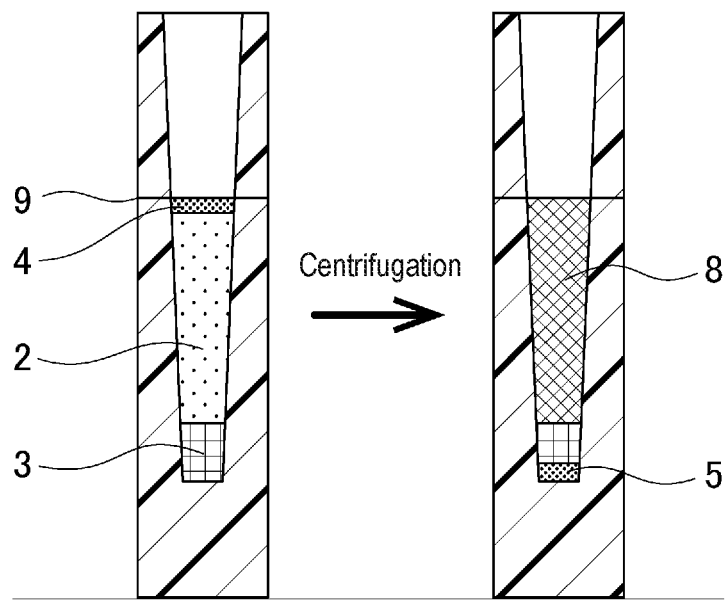
FIG. 2 is a schematic view similar to FIG. 1. Specifically, FIG. 2 schematically shows the blood analysis structure in which the gelling agent for plasma separation is accommodated immediately beneath the dilution buffer (a type of a structure wherein the gelling agent for plasma separation is enclosed within the bottom portion) before and after the application of centrifugal force.

In consideration of the above circumstances, the present inventors found a technique for separately storing blood cells and diluted plasma by adding a blood dilution buffer to a minute amount of collected blood (about 20 to 100 μL), and effectively separating blood cells and dilution plasma using the polymer gelling agent in a container containing a blood dilution buffer in which a blood dilution buffer is contained In one preferred embodiment of the present invention, a container for blood dilution and storage 1 is prepared as shown in FIGS. 1 and 2. The container for blood dilution and storage 1 accommodates a predetermined amount of a dilution buffer 2 and a polymer gelling agent for plasma separation 3, thereby constituting a blood analysis structure.

The dilution buffer 2 is intended to dilute plasma in collected blood 4.

The specific gravity of the polymer gelling agent for plasma separation 3 is adjusted to fall between the specific gravity of blood cells 5 in the blood 4 and that of plasma diluted with the dilution buffer 2.

In the above case, the blood dilution buffer 2 and the polymer gelling agent for plasma separation 3 coexist in the container 1 and are allowed to come into direct contact with each other, although they are not allowed to mix. That is, the blood dilution buffer 2 and the polymer gelling agent for plasma separation 3 separately occupy different regions in the container 1.

In one embodiment, the dilution buffer 2 forms a layer beneath a sealing cap 7 for the upper opening 6 of the container 1, and the polymer gelling agent for plasma separation 3 forms a layer thereunder.

In another embodiment, the polymer gelling agent for plasma separation 3 forms a layer on the upper opening side, and the dilution buffer 2 forms a layer thereunder.

In one embodiment, the dilution buffer 2 forms a layer beneath the upper opening 6 as shown in FIG. 2, and the polymer gelling agent for plasma separation 3 forms a layer thereunder.

Figure 3:
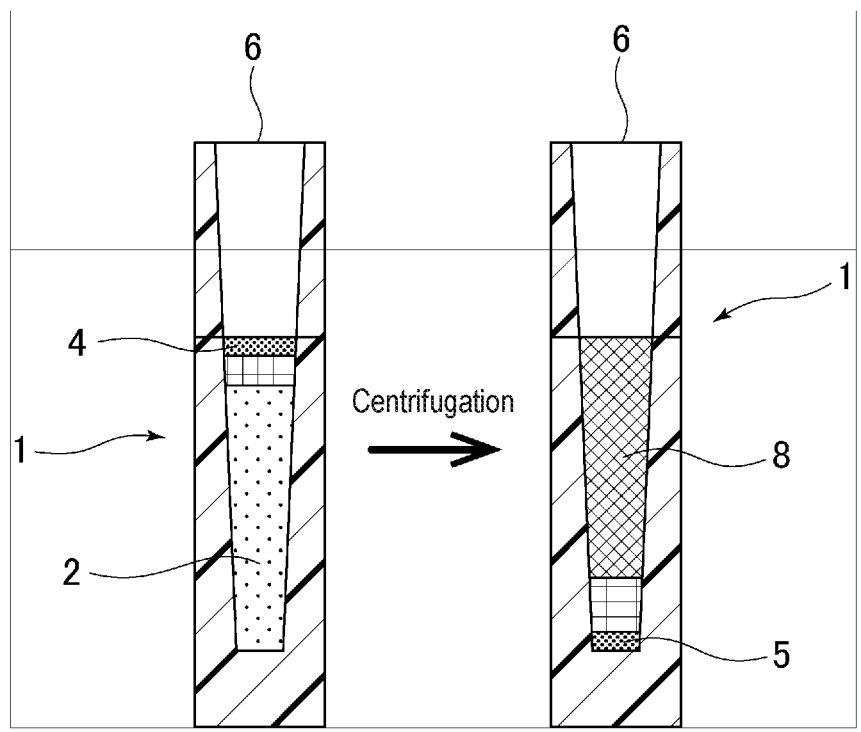
FIG. 3 is a schematic view similar to FIG. 1. Specifically, FIG. 3 schematically shows the blood analysis structure in which the gelling agent for plasma separation is accommodated immediately above the dilution buffer (a type of a structure wherein the gelling agent for plasma separation is enclosed within the portion above the dilution buffer) before and after the addition of the centrifugal force.

In another embodiment, the polymer gelling agent for plasma separation 3 forms a layer on the upper opening side as shown in FIG. 3, and the dilution buffer forms a layer thereunder.

Then, a collected blood sample is introduced from the upper opening 6 into the container 1 accommodating the both the agent and the buffer. A centrifugal force is applied to the container 1 in a downward direction. This results in separation of the blood sample into a layer of blood cells 5 and a layer of plasma 8 diluted with the dilution buffer 2. In such case, the centrifugal force is applied to the container at about 1300 G for about 10 minutes. In addition, the container 1 is allowed to accommodate the dilution buffer 2, the polymer gelling agent for plasma separation 3, and a collected blood sample, the container 1 is set in a portable centrifuge (not shown), and then a centrifugal force is applied to the container 1 for blood dilution and storage in a downward direction.

In a preferred embodiment, the specific gravity of the dilution buffer 2 is lower than the specific gravity of plasma. The specific gravity of the plasma 8 diluted with the dilution buffer 2 becomes about 1.012 to 1.014. That is, the difference in specific gravity between the blood cells and the diluted plasma is increased. Therefore, the separation of diluted blood cells and diluted plasma becomes easier than the separation of undiluted blood cells 5 (which have a specific gravity of about 1.095) and undiluted plasma (which have a specific gravity of about 1.027). A diluent used herein is a liquid having a specific gravity of about 1.0106 and an osmotic pressure of about 285 mOsm/L, thus making such diluent isotonic with blood. When the dilution buffer has a high osmotic pressure, the osmotic pressure is about 500 mOsm/L and the specific gravity is about 1.011. Preferably, the container for accommodating a blood sample is made of transparent plastic.

Preferably, a mark 9 is made on the container 1, and the mark indicates that the container is filled with a predetermined amount of blood. In such case, it is preferable to make such mark on the outer circumference of the container containing the blood dilution buffer at a location such that the mark indicates that the container is filled with 20 to 100 μL (e.g., about 65 μL) of blood, thereby making it possible to visually confirm the collection of a predetermined amount of blood.

Figure 4:
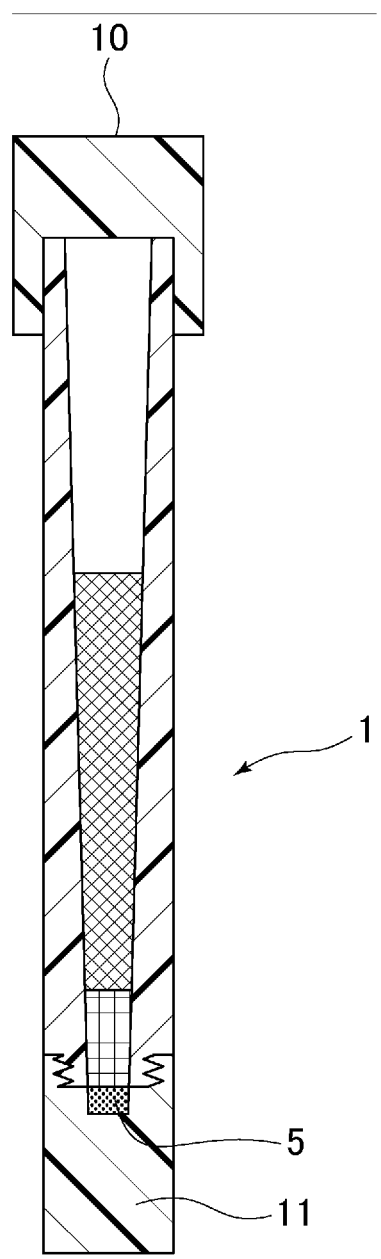
FIG. 4 schematically shows a cross-sectional view of the container for blood dilution and storage that constitutes the blood analysis structure. The container for blood dilution is configured so as to have a screw-type bottom cap that can be opened and closed at the bottom portion in which blood cells become sedimented via centrifugation and can thus be used for a test sample.

As shown in FIG. 4, preferably, the upper opening of the container can be opened or closed using a tightly sealable cap, such as a screw-type top cap 10, which improves sealing performance. Further, the bottom portion of the container 1 may be openable/closable or detachable using a screw-type top cap 11 in a similar manner. Such configuration allows a centrifugal force to be applied to the container 1 containing the blood dilution buffer, thereby removing sedimented blood cells 5 adhering to the bottom portion of the container 1 and allowing such cells to be used for an examination.

For example, the container 1 has a cylindrical shape and is 14±2 mm in outer diameter and 75±5 mm in height. It is configured so as to have a bottom portion provided with a detachable cylindrical bottom cap 11 which is 14±2 mm in outer diameter and 25±2 mm in height. The inner space of the container 1 is shaped such that it has an uppermost inner diameter of 10 mm, a lowest bottom inner diameter of 5 mm, and a depth from the uppermost portion to the lowest bottom portion of 30 mm, and the shape of the inner space tapers from the uppermost portion toward the lowest bottom portion.

In such case, the inner portion of the blood collection container has an upper inner circle diameter of 10 mm, a depth of 30 mm, and an inner bottom diameter of 5 mm. It has an inverted conical shape that tapers downward toward the bottom.

The composition of the polymer gel for plasma separation comprises, for example, a thixotropic-gel-type separating agent obtained by kneading a cyclopentadiene resin, dibenzylidene sorbitol, silica, and phthalic acid (2-ethylhexyl)

(Patent Publication (Kokai) No. 117-294516 A (1995)). Alternatively, it may comprise a similar thixotropic-gel-type separating agent.

The physical properties of the polymer gel for plasma separation are as follows: HLB value: 4.02 to 9.0; specific gravity: 1.02 to 1.08 at 25° C.; and molecular weight distribution determined by the GPC method for molecular weight: 700-850.

In a preferred embodiment, such gel-type separating agent is characterized in that diluted plasma is separated from blood cells under conditions in which a centrifugal force of 1,300 G is applied for 10 minutes.

Further, according to the present invention, a method for centrifuging a sample obtained by diluting a minute amount of blood with a dilution buffer using a polymer gel for plasma separation is provided.

EXAMPLES

Examples of biochemical examination employing the container for blood dilution and storage containing the gelling agent for plasma separation are described below.

Data provided below indicate the correlation for each test item between measured values for plasma obtained by centrifuging brachial vein blood to which EDTA had been added, which was used as a sample, and values obtained by multiplying the measured values by the dilution factor.

Figure 5:
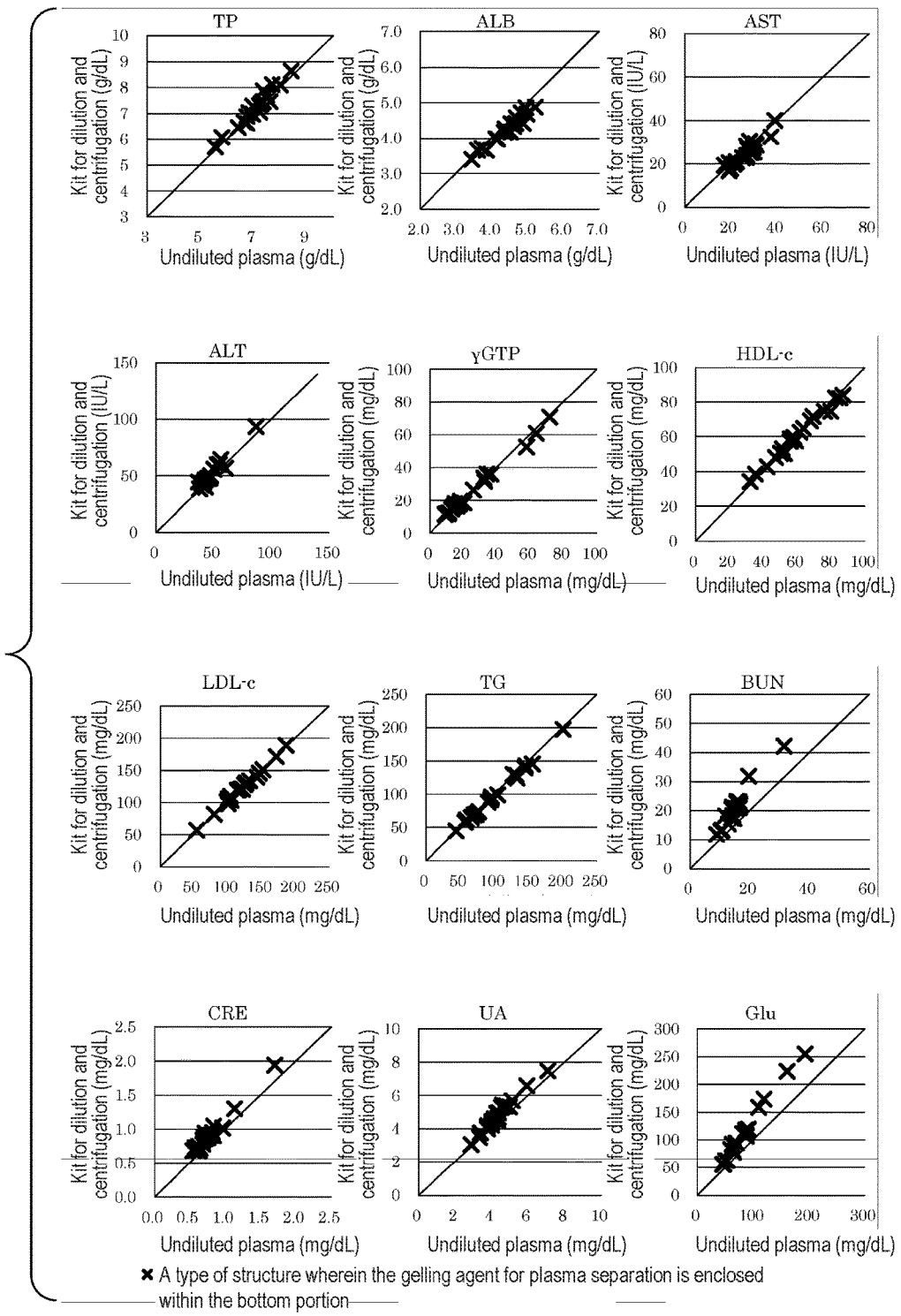
FIG. 5 shows diagrams of data on the correlation between undiluted venous plasma (x) and plasma mixed with a type of a structure wherein the gelling agent for plasma separation is enclosed within the bottom portion (y).

Table 1 lists statistical data on the correlation between undiluted plasma (x) and plasma from a type of a structure wherein the gelling agent for plasma separation is enclosed within the bottom portion (the gelling agent being disposed on the lower side of the dilution buffer layer) (y),. FIG. 5 shows correlation diagrams for such data.

TABLE 1

A type of a structure wherein the gelling agent for plasma separation is enclosed within the bottom portion

| Item | Regression equation | Correlation coefficient | Number of cases |
| --- | --- | --- | --- |
| TP | y = 1.02x − 0.03 | 0.969 | 20 |
| ALB | y = 0.84x + 0.84 | 0.972 | 20 |
| AST | y = 0.91x + 0.60 | 0.929 | 20 |
| ALT | y = 1.07x − 0.62 | 0.968 | 20 |
| γGTP | y = 0.92x + 2.12 | 0.997 | 20 |
| HDL-c | y = 0.91x + 5.30 | 0.993 | 20 |
| LDL-c | y = 0.98x + 2.74 | 0.996 | 20 |
| TG | y = 0.96x + 0.33 | 0.997 | 20 |
| BUN | y = 1.42x − 0.90 | 0.961 | 20 |
| CRE | y = 1.09x + 0.06 | 0.985 | 20 |
| UA | y = 1.10x − 0.04 | 0.982 | 20 |
| Glu | y = 1.41x − 7.48 | 0.992 | 20 |

Figure 6:
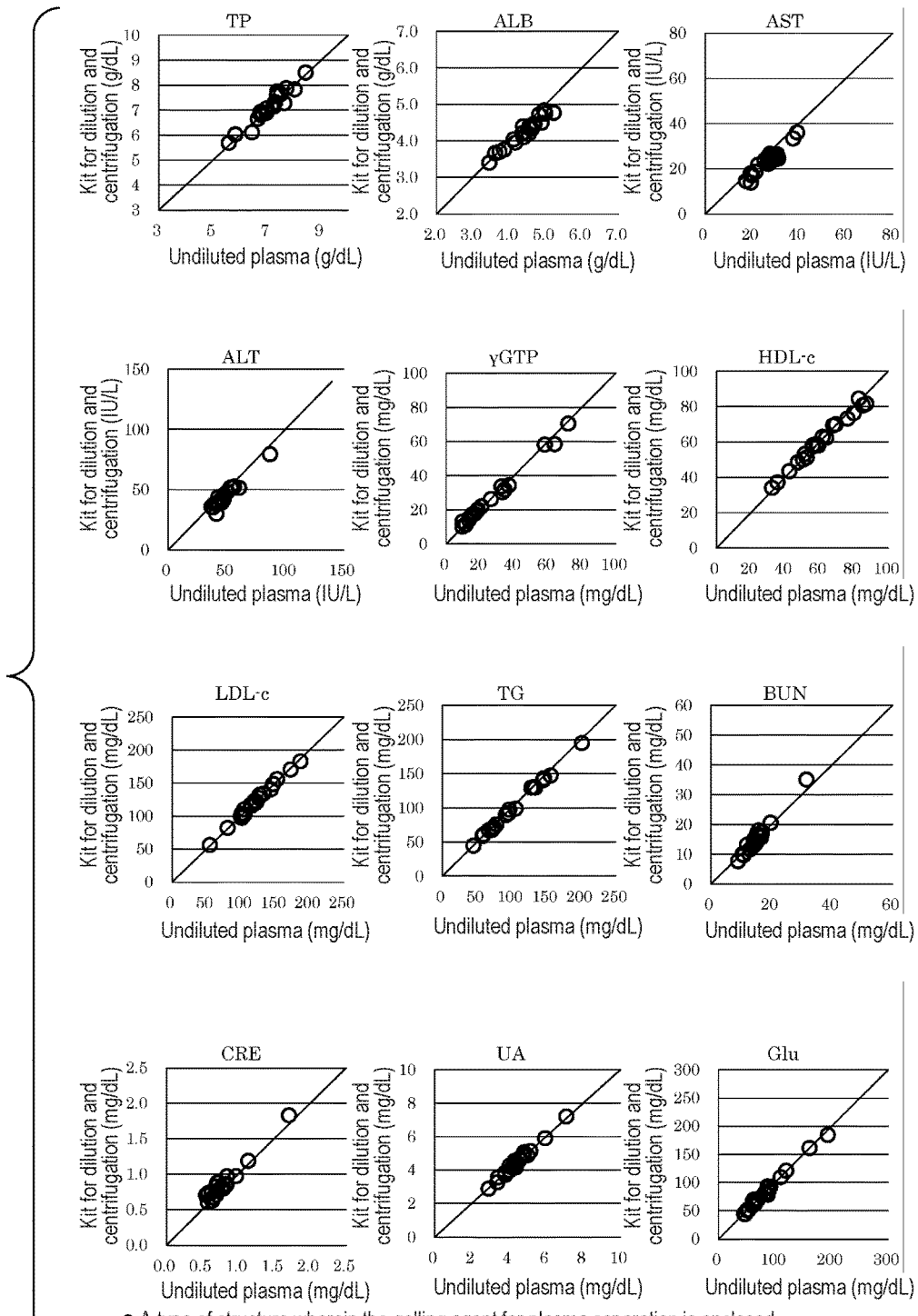
FIG. 6 shows diagrams of data on the correlation between undiluted venous plasma (x) and plasma mixed with a type of a structure wherein the gelling agent for plasma separation is enclosed within the portion above the dilution buffer (y).

Table 2 lists statistical data on the correlation between undiluted plasma (x) and plasma from a type of a structure wherein the gelling agent for plasma separation is enclosed within the portion above the dilution buffer (the gelling agent being disposed on the upper side of the layer of the dilution buffer) (y),. FIG. 6 shows correlation diagrams for such data.

TABLE 2

A type of a structure wherein the gelling agent for plasma separation is enclosed within the portion above the dilution buffer

| Item | Regression equation | Correlation coefficient | Number of cases |
| --- | --- | --- | --- |
| TP | y = 0.98x + 0.14 | 0.961 | 20 |
| ALB | y = 0.81x + 0.67 | 0.970 | 20 |
| AST | y = 0.92x − 1.32 | 0.958 | 20 |
| ALT | y = 0.90x + 0.72 | 0.966 | 20 |
| γGTP | y = 0.93x + 1.99 | 0.996 | 20 |
| HDL-c | y = 0.90x + 5.30 | 0.993 | 20 |
| LDL-c | y = 0.98x + 2.74 | 0.996 | 20 |
| TG | y = 0.96x + 1.50 | 0.998 | 20 |
| BUN | y = 1.20x − 2.88 | 0.961 | 20 |
| CRE | y = 1.00x + 0.07 | 0.969 | 20 |
| UA | y = 1.02x − 0.07 | 0.992 | 20 |
| Glu | y = 0.97x + 2.09 | 0.995 | 20 |

As shown in Table 1 and Table 2, a highly favorable correlation result was confirmed for plasma. Thus, it is possible to obtain values comparable to the measurement values obtained using undiluted plasma as a sample with the diluted plasma separation method using the container for blood dilution and storage containing the gelling agent for plasma separation.

INDUSTRIAL APPLICABILITY

The above method for collecting a minute amount of blood is not limited in terms of time or location for blood collection. Therefore, it can be used in practice at times of disaster and for telemedicine, health management, and the like if there is insufficient time to go to a medical institution, thereby allowing early detection for individuals in presymptomatic states. Accordingly, the method can contribute to health care cost reduction.

REFERENCE SIGNS LIST

1: container for blood dilution and storage
2: dilution buffer
3: polymer gelling agent for plasma separation
4: sample blood
5: blood cell
6: upper opening
7: sealing cap
8: diluted plasma
9: mark
10: screw-type top cap
11: screw-type bottom cap

We claim:
1. A blood analysis structure for accommodating a bioanalytical sample prepared by diluting a minute amount of collected blood, comprising:
   a dilution buffer for diluting plasma in the collected blood;
   a polymer gel for plasma separation for separating the diluted plasma from blood cells in the collected blood;
   a container for blood dilution and storage for accommodating the dilution buffer and the polymer gel for plasma separation and receiving and accommodating the collected blood so as to store the collected blood; and
   a sealing cap for enclosing the blood to be introduced from the upper opening of the container for blood dilution and storage together with the dilution buffer and the polymer gel for plasma separation into the container for blood dilution and storage, wherein the dilution buffer and the polymer gel for plasma separation are allowed to separately form independent layers disposed in the vertical direction within the inner space of the container for blood dilution and storage, wherein the collected blood is introduced from the upper opening and a centrifugal force is applied to the container for blood dilution and storage in a downward direction, thereby allowing a plasma layer of the dilution buffer containing plasma of the collected and diluted blood, a layer of the polymer gel for plasma separation, and a layer of the blood cells to be separately formed as independent layers in the container for blood dilution and storage, wherein the specific gravity of the dilution buffer is lower than that of the plasma, and wherein the specific gravity of the plasma layer of the diluted plasma in the collected blood is approximately 1.012 to 1.014.

2. The blood analysis structure according to claim 1, wherein the specific gravity of the polymer gel for plasma separation is lower than that of the blood cells and higher than that of the plasma layer.

3. The blood analysis structure according to claim 1, wherein the dilution buffer has a specific gravity of approximately 1.0106 and an osmotic pressure of 285 mOsm/L, thus making the dilution buffer approximately isotonic with the blood.

4. The blood analysis structure according to claim 1, wherein the dilution buffer has a specific gravity of approximately 1.011 and an osmotic pressure of approximately 500 mOsm/L, which is higher than that of the blood.

5. The blood analysis structure according to claim 1, wherein the dilution buffer forms a layer beneath the sealing cap for the upper opening, and the polymer gelling agent for plasma separation forms a layer thereunder.

6. The blood analysis structure according to claim 1, wherein the polymer gelling agent for plasma separation forms a layer on the upper opening side, and the dilution buffer forms a layer thereunder.

7. The blood analysis structure according to claim 1, wherein the container for blood dilution and storage is made of a transparent plastic.

8. The blood analysis structure according to claim 1, wherein a mark is made on the container for blood dilution and storage, and the mark indicates that the container for blood dilution and storage is filled with a predetermined amount of blood.

9. The blood analysis structure according to claim 1, wherein the container for blood dilution and storage is provided with a screw-type cap that is able to seal the upper opening.

10. The blood analysis structure according to claim 1, wherein the bottom portion of the container for blood dilution and storage is openable and closable or is detachable.

11. The blood analysis structure according to claim 10, wherein the container for blood dilution and storage has a cylindrical shape, is approximately 14 mm in outer diameter and approximately 75 mm in height, and is provided with a detachable bottom cap which is approximately 14 mm in outer diameter and approximately 25 mm in height and located at the bottom portion of the container for blood dilution and storage.

12. The blood analysis structure according to claim 1, wherein the inner space of the container for blood dilution and storage is shaped such that it has an upper end having an inner diameter of approximately 10 mm and a lower end having an inner diameter of approximately 5 mm, the depth from the upper end to the lower end is approximately 30 mm, and the inner diameter gradually decreases from the upper end toward the lower end.

13. A blood analysis structure for accommodating a bioanalytical sample prepared by diluting a minute amount of collected blood, comprising:

a dilution buffer containing an internal standard for diluting plasma in the collected blood;

a polymer gel for plasma separation for separating the diluted plasma from blood cells in the collected blood;

a container for blood dilution and storage for accommodating the dilution buffer and the polymer gel for plasma separation and receiving and accommodating the collected blood so as to store the collected blood; and a sealing cap for enclosing the blood to be introduced from the upper opening of the container for blood dilution and storage together with the dilution buffer and the polymer gel for plasma separation into the container for blood dilution and storage, wherein the dilution buffer and the polymer gel for plasma separation are allowed to separately form independent layers disposed in the vertical direction within the inner space of the container for blood dilution and storage, wherein the collected blood is introduced from the upper opening and a centrifugal force is applied to the container for blood dilution and storage in a downward direction, thereby allowing a plasma layer of the dilution buffer containing plasma of the collected and diluted blood, a layer of the polymer gel for plasma separation, and a layer of the blood cells to be separately formed as independent layers in the container for blood dilution and storage, wherein the specific gravity of the dilution buffer is lower than that of the plasma, and wherein the specific gravity of the plasma layer of the diluted plasma in the collected blood is approximately 1.012 to 1.014.

14. A method for diluted blood separation for accommodating a bioanalytical sample prepared by diluting a minute amount of collected blood to separate diluted plasma from blood cells, comprising the steps of:

preparing a dilution buffer for diluting plasma in the collected blood;

preparing a polymer gel for plasma separation for separating the diluted plasma from blood cells in the collected blood;

preparing a container for blood dilution and storage for accommodating the dilution buffer and the polymer gel for plasma separation and receiving and accommodating the collected blood so as to store the collected blood;

preparing a sealing cap for enclosing the blood to be introduced from the upper opening of the container for blood dilution and storage together with the dilution buffer and the polymer gel for plasma separation into the container for blood dilution and storage;

introducing the dilution buffer and the polymer gel for plasma separation in a manner such that they separately form independent layers disposed in the vertical direction within the inner space of the container for blood dilution and storage;

introducing the collected blood from the upper opening; and applying a centrifugal force to the container for blood dilution and storage in a downward direction, thereby allowing a plasma layer of the dilution buffer containing plasma of the collected and diluted blood, a layer of the polymer gel for plasma separation, and a layer of the blood cells to be separately formed as independent layers in the container for blood dilution and storage, wherein the specific gravity of the plasma layer of the diluted plasma in the collected blood is approximately 1.012 to 1.014.

15. A method for diluted blood separation for accommodating a bioanalytical sample prepared by diluting a minute amount of collected blood to separate diluted plasma from blood cells, comprising the steps of:

preparing a dilution buffer containing an internal standard for diluting plasma in the collected blood;

preparing a polymer gel for plasma separation for separating the diluted plasma from blood cells in the collected blood;

preparing a container for blood dilution and storage for accommodating the dilution buffer and the polymer gel for plasma separation and receiving and accommodating the collected blood so as to store the collected blood;

preparing a sealing cap for enclosing the blood to be introduced from the upper opening of the container for blood dilution and storage together with the dilution buffer and the polymer gel for plasma separation into the container for blood dilution and storage;

introducing the dilution buffer and the polymer gel for plasma separation in a manner such that they separately form independent layers disposed in the vertical direction within the inner space of the container for blood dilution and storage;

introducing the collected blood from the upper opening; and applying a centrifugal force to the container for blood dilution and storage in a downward direction, thereby allowing a plasma layer of the dilution buffer containing plasma of the collected and diluted blood, a layer of the polymer gel for plasma separation, and a layer of the blood cells to be separately formed as independent layers in the container for blood dilution and storage, wherein the specific gravity of the plasma layer of the diluted plasma in the collected blood is approximately 1.012 to 1.014.

* * * * *